US00PP31960P2

(12) United States Plant Patent
Nelson et al.

(10) Patent No.: US PP31,960 P2
(45) Date of Patent: Jul. 14, 2020

(54) STRAWBERRY PLANT NAMED 'BG-10.3181'

(50) Latin Name: *Fragaria ananassa*
Varietal Denomination: BG-10.3181

(71) Applicant: BERRY GENETICS, INC., Freedom, CA (US)

(72) Inventors: Steven D. Nelson, Watsonville, CA (US); Michael D. Nelson, Watsonville, CA (US); Leo W. Stoeckle, Moorpark, CA (US)

(73) Assignee: BERRY GENETICS, INC., Freedom, CA (US)

( * ) Notice: Subject to any disclaimer, the term of this patent is extended or adjusted under 35 U.S.C. 154(b) by 0 days.

(21) Appl. No.: 16/602,400

(22) Filed: Sep. 30, 2019

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

*Primary Examiner* — Kent L Bell
(74) *Attorney, Agent, or Firm* — Foley & Lardner LLP

(57) ABSTRACT

This invention relates to a new and distinct variety of strawberry plant named 'BG-10.3181'. This new strawberry plant named 'BG-10.3181' is primarily adapted to the growing conditions of the central coast of California, and is primarily characterized by its very large fruit size, very good fruit flavor with very firm flesh, early time of first flower and fruit, medium plant size with dark green foliage, and fruiting truss flowers typically not visible above the foliage.

4 Drawing Sheets

Latin name of the genus and species of the plant claimed: *Fragaria ananassa.*

Variety denomination: 'BG-10.3181'.

BACKGROUND OF THE INVENTION

The present invention relates to a new and distinct strawberry variety named 'BG-10.3181'. This new variety is a result of a controlled cross made in 2010 in an ongoing breeding program between strawberry selection designated 'BG-4.378' (unpatented) as the seed (female) parent, and strawberry variety designated 'BG-4.370' (U.S. Plant Pat. No. 27,441) as the pollen (male) parent. The variety is botanically known as *Fragaria ananassa.*

The seedling resulting from the aforementioned cross was selected from a controlled breeding plot in Ventura County, Calif. in the winter of 2012. After its selection, the new variety was asexually propagated by stolons in both Siskiyou County, Calif. and San Joaquin County, Calif. The new variety was extensively tested over the next several years in fruiting fields in Ventura County, Calif. This propagation has demonstrated that the combination of traits disclosed herein as characterizing the new variety are fixed and remain true-to-type through successive generations of asexual reproduction.

BRIEF SUMMARY OF THE INVENTION

'BG-10.3181' is primarily adapted to the climate and growing conditions of the central coast of California. The nearby Pacific Ocean provides the humidity and moderate temperatures needed to produce a strong, vigorous plant and maintain fruit quality during the winter and spring production months.

The following traits have been repeatedly observed and are determined to be unique characteristics of 'BG-10.3181', which in combination distinguish this strawberry plant as a new and distinct variety:

1. Very large fruit size;
2. Very good fruit flavor with very firm flesh;
3. Early time of first flower and fruit;
4. Medium plant size with dark green foliage; and
5. Fruiting truss flowers typically not visible above the foliage.

The strawberry variety that is believed to be most closely related to the new variety 'BG-10.3181' is 'BG-3.324' (U.S. Plant Pat. No. 23,256). In side-by-side comparisons to the similar strawberry variety 'BG-3.324', 'BG-10.3181' differs by the following combination of characteristics as described in Table 1.

TABLE 1

| Characteristic | 'BG-10.3181' | 'BG-3.324' (U.S. Plant Pat. No. 23,256) |
|---|---|---|
| Fruit: marketable yield (gm/plt) | 1,157 | 1,049 |
| Fruit: season average size (gm) | 30.9 | 29.1 |
| Fruit: flavor | Very good | Good |
| Fruit: Difference in shape between primary and secondary | Slight | Moderate |
| Fruit: firmness of flesh | Very firm | Ranges from firm to very firm |
| Fruit: expression of hollow center | Weak | Strong |
| Terminal leaflet: shape of base | Acute | Obtuse |
| Foliage: color of upper surface | Dark green | Ranges from light to medium yellow green |
| Fruiting truss: position relative to foliage | Below | Ranges from even with to above |
| Fruiting truss: pubescence | Weak | Medium |
| Disease reactions: Fusarium wilt | Resistant | Susceptible |

For identification, a series of molecular markers have been determined for this new variety.

'BG-10.3181' differs from its parents, 'BG-4.378' and 'BG-4.370' by the following combination of characteristics as described in Tables 2 and 3.

TABLE 2

| Characteristic | 'BG-10.3181' | 'BG-4.378' (unpatented) |
|---|---|---|
| Fruit: size | Very large | Medium |
| Fruit: flavor | Very good | Fair |
| Fruit: insertion of achenes | Ranges from level with to below the surface | Below the surface |
| Plant: vigor | Medium | Large |

TABLE 3

| Characteristic | 'BG-10.3181' | 'BG-4.370' (U.S. Plant Pat. No. 27,441) |
|---|---|---|
| Fruit: marketable yield | Ranges from medium to high | Medium |
| Plant: vigor | Medium | Small |
| Fruiting truss: position relative to foliage | Below | Above |
| Disease reactions: Fusarium wilt | Resistant | Susceptible |

BRIEF DESCRIPTIONS OF THE PHOTOGRAPHS

The accompanying color photographs illustrate the overall appearance of typical specimens of the new strawberry variety 'BG-10.3181' at various stages of development, as true as it is reasonably possible with color reproductions of this type. Color in the photographs may differ slightly from the color value cited in the botanical descriptions which accurately describe the color of 'BG-10.3181'. The depicted plant and plant parts of the new strawberry variety 'BG-10.3181' are approximately six months old. The photographs were taken in Ventura County, Calif.

DETAILED BOTANICAL DESCRIPTION

Figure 1:
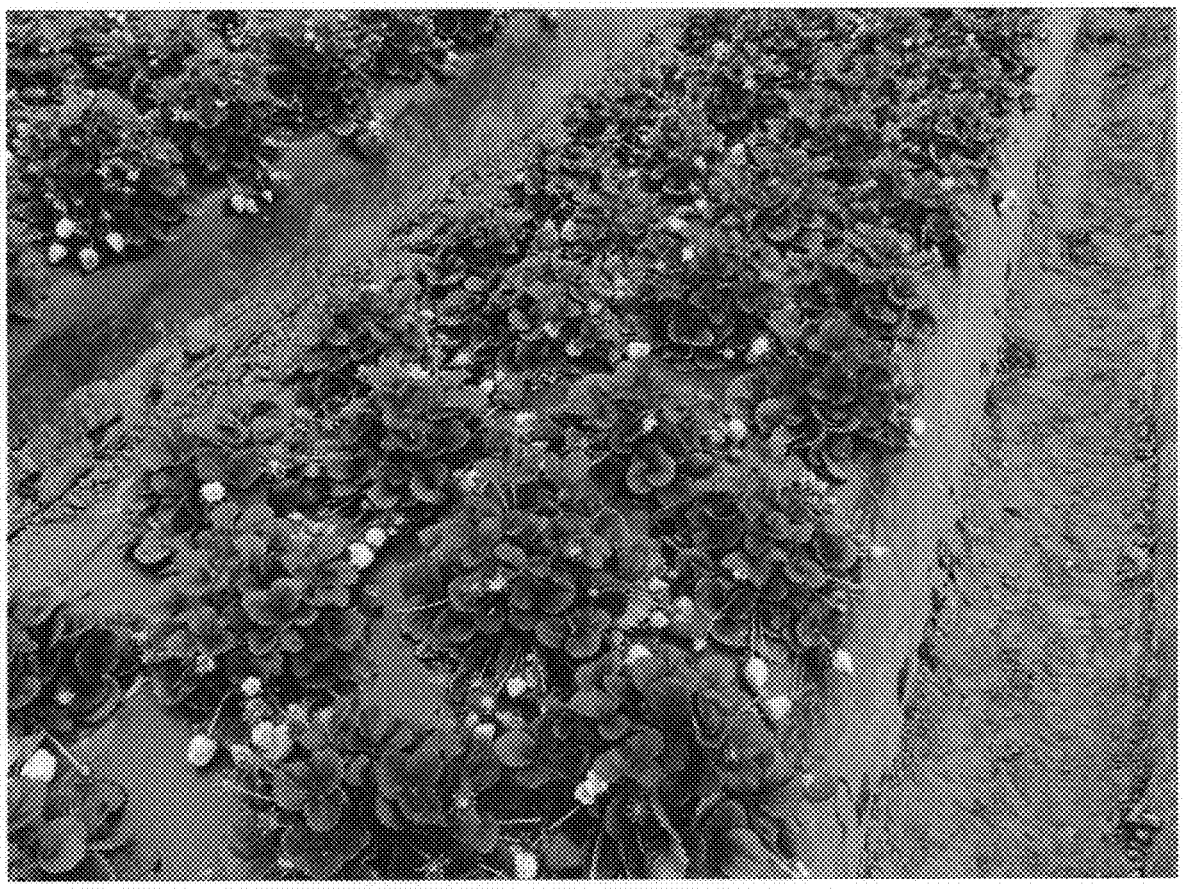
FIG. 1 shows typical fruiting field characteristics of 'BG-10.3181', taken in the month of March 2019.
Figure 2:
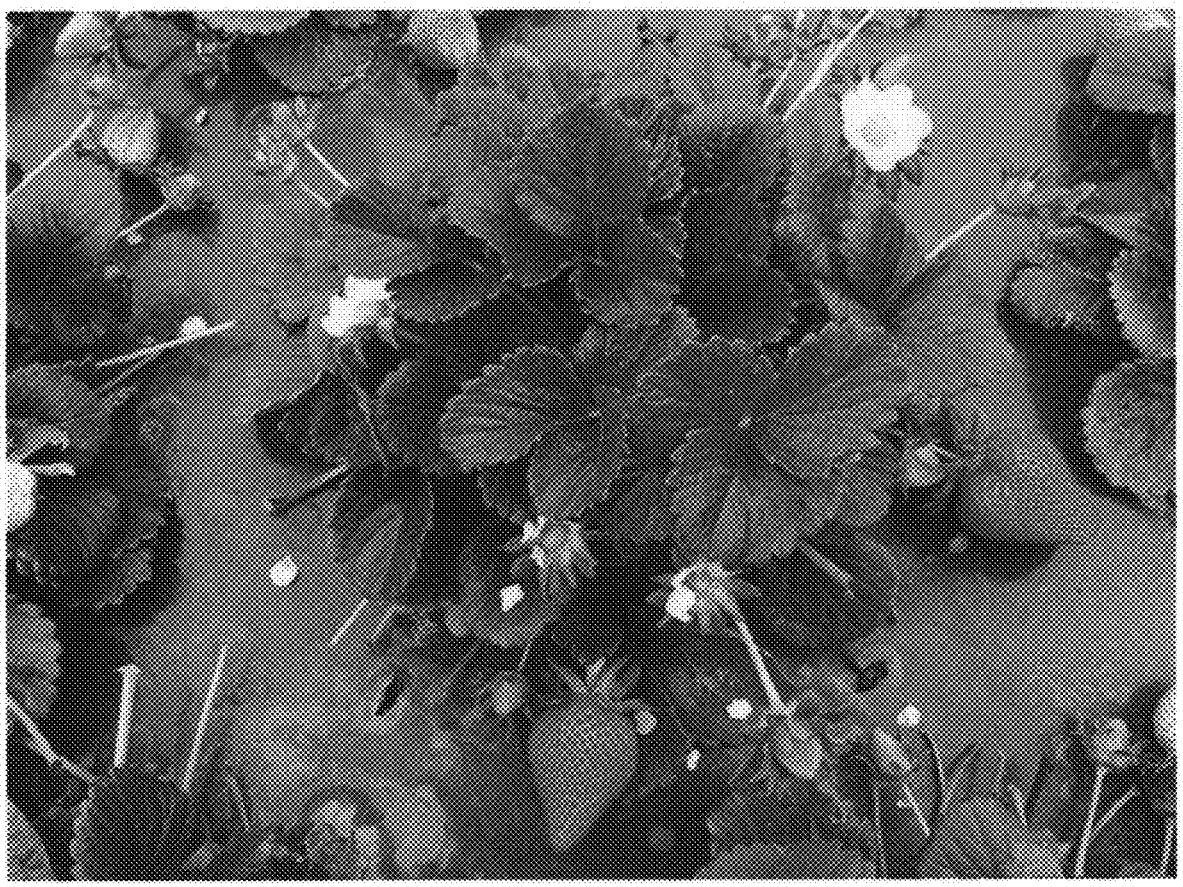
FIG. 2 shows a close-up view of a typical plant of 'BG-10.3181', taken in the month of March 2019.
Figure 3:
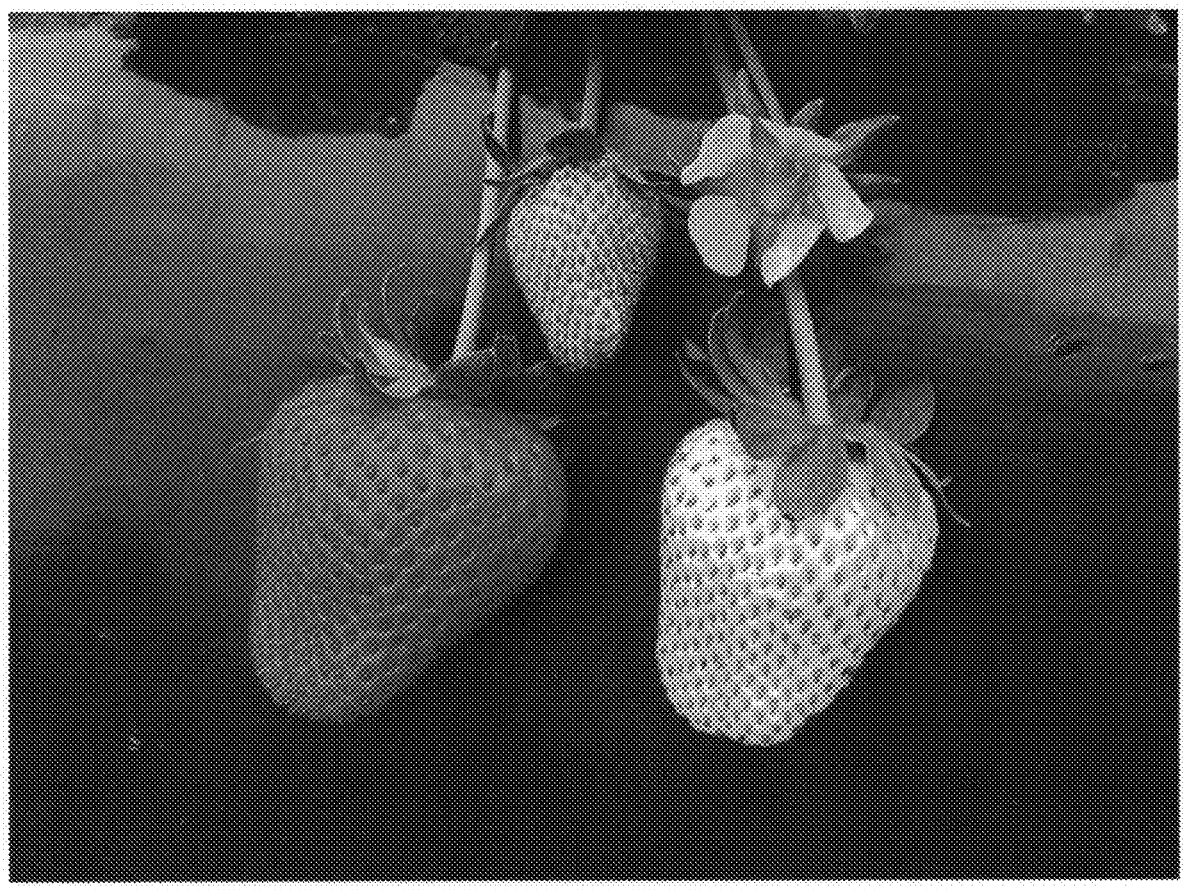
FIG. 3 shows typical mature and immature field fruit of 'BG-10.3181', taken in the month of March 2019.
Figure 4:
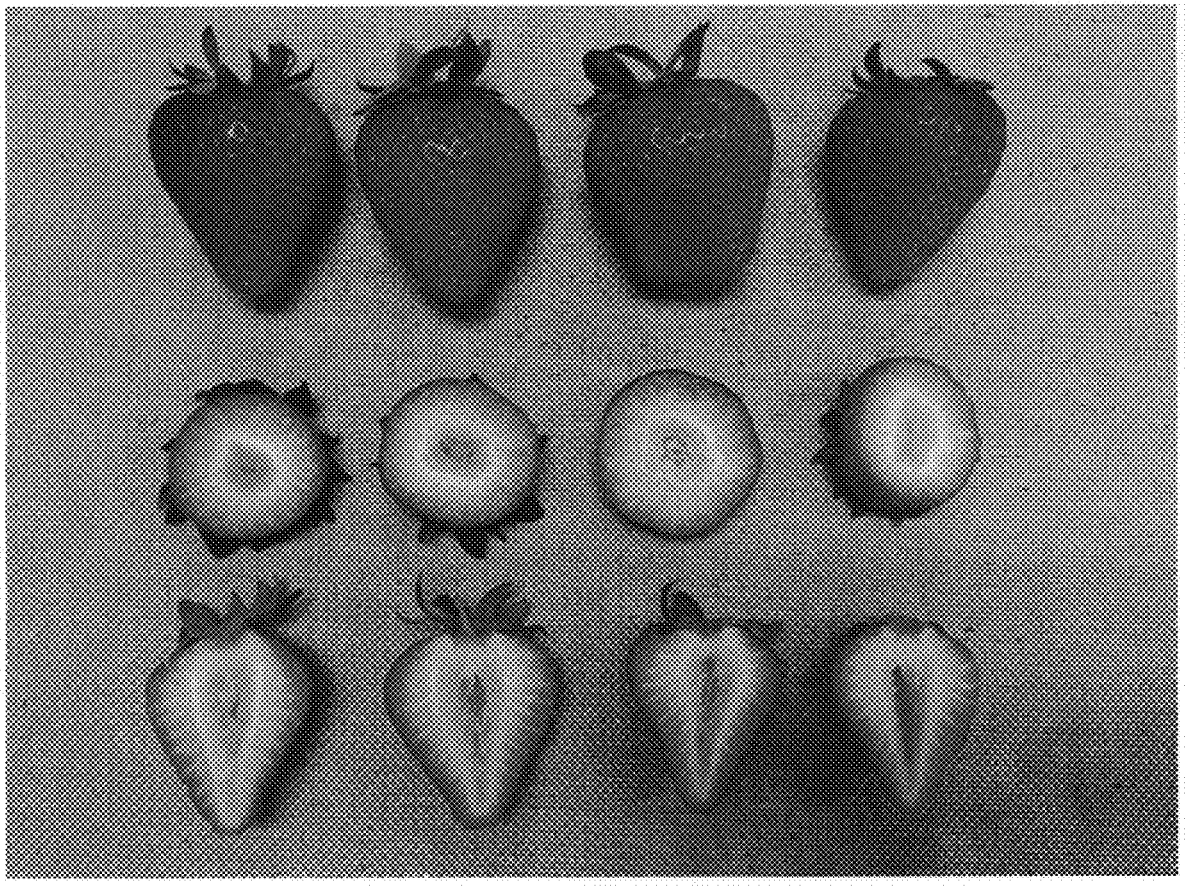
FIG. 4 shows typical internal and external mature fruit characteristics of 'BG-10.3181', taken in the month of March 2019.

The new variety 'BG-10.3181' has not been observed under all possible environmental conditions. The characteristics of the new variety 'BG-10.3181' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'BG-10.3181', unless otherwise noted, are based on observations taken during the 2019 growing season in Ventura County, Calif. These measurements and ratings were taken from plants of 'BG-10.3181' dug from a high-elevation nursery located in Siskiyou County, Calif. during early October 2018 and planted approximately four to five days later in Ventura County, Calif. The approximate age of the observed plants is six months. Yield observations including average weight and marketable yield, along with fruit quality characteristics including soluble solids, are averaged from five years of data collected from the 2014 through 2018 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London (2007).

The following characteristics describe fruit, plant, stolon, foliage, fruiting truss, flower, reproductive organs and pest and disease characteristics of the new strawberry 'BG-10.3181'.

Fruit characteristics:

*Color of mature fruit*.—RHS 47B (ranges from orange red to red).

*Color of internal flesh* (*excluding core*).—RHS 34A (medium red).

*Color of core*.—RHS 39B (medium red).

*Average length* (*cm*).—4.6.

*Average width* (*cm*).—4.0.

*Size*.—Very large.

*Average length/width ratio*.—1.16 (slightly longer than broad).

*Average calyx diameter* (*cm*).—4.3.

*Season average weight* (*gm*).—30.9.

*Achene color, shaded side*.—RHS 153C (yellow green group).

*Achene color, sun-exposed side*.—RHS 184A (greyed purple group).

*Average achene weight* (*mg*).—0.44.

*Average achenes per berry*.—377.

*Season marketable yield* (*gm/plant*).—1,157.

*Predominant shape*.—Conical.

*Difference in shape between primary and secondary fruit*.—Slight.

*Band without achenes*.—Medium.

*Evenness of surface*.—Slightly uneven.

*Evenness of color*.—Even or very slightly uneven.

*Glossiness*.—Ranges from medium to strong.

*Insertion of achenes*.—Ranges from below surface to level with surface.

*Position of calyx attachment*.—Ranges from inserted to level.

*Attitude of sepals*.—Outward.

*Size of calyx in relation to fruit diameter*.—Slightly larger.

*Adherence of calyx* (*when fully ripe*).—Strong.

*Firmness of flesh*.—Ranges from firm to very firm.

*Distribution of red color of the flesh*.—Marginal and central.

*Hollow center expression*.—Ranges from weak to moderate.

*Flavor*.—Very good.
*Soluble solids* (*% brix*).—8.9.
*Time of first flowering*.—Early (late November in Ventura County, Calif.).
*Time of first fruit*.—Early (late December in Ventura County, Calif.).
*Harvest period*.—Late December to May (in Ventura County, Calif.).
*Harvest maturity*.—Early season (March).
*Type of bearing*.—Not remontant.

Plant characteristics:
*Average height* (*cm*).—18.2.
*Average spread* (*cm*).—27.8.
*Size*.—Medium.
*Habit*.—Upright.
*Density*.—Medium.
*Vigor*.—Medium.

Stolon characteristics:
*Color*.—RHS 146D (yellow green group).
*Anthocyanin coloration*.—RHS 182D (greyed red group).
*Anthocyanin intensity*.—Weak.
*Pubescence*.—Sparse.
*Attitude of hairs*.—Upward.
*Average quantity in nursery* (*per square foot*).—5 to 6 (medium).
*Average diameter at the bract* (*mm*).—3.1 (medium).

Terminal leaflet characteristics:
*Average length* (*cm*).—5.6.
*Average width* (*cm*).—5.0.
*Average area terminal* ($cm^2$).—27.7.
*Average length/width ratio*.—1.12 (longer than broad).
*Shape of base*.—Acute.
*Margins* (*shape of teeth*).—Obtuse (serrate to crenate).
*Average serrations per leaf*.—15.9.

Foliage characteristics:
*Color of upper surface*.—RHS N137A (dark green).
*Color of underside*.—RHS 147C (yellow green group).
*Number of leaflets*.—3.
*Leaf size*.—Ranges from medium to small.
*Average length* (*cm*).—8.0.
*Average width* (*cm*).—10.8.
*Average area foliage* ($cm^2$).—87.7.
*Shape in cross section*.—Slightly concave to flat.
*Interveinal blistering*.—Ranges from medium to strong.
*Leaf glossiness*.—Ranges from medium to strong.
*Leaf variegation*.—Absent.

Petiole characteristics:
*Petiole color*.—RHS 145A (yellow green group).
*Average length* (*cm*).—10.6.
*Average diameter* (*mm*).—2.7.
*Petiolule color*.—RHS 145A (yellow green group).
*Petiolule average length* (*mm*).—4.0.
*Attitude of hairs*.—Slightly outward.
*Frequency of bract leaflets*.—Ranges from few to none (0% occurrence).
*Size of bract leaflets*.—N/A.
*Pubescence*.—Moderate.

Stipule characteristics:
*Color*.—RHS 145C (yellow green group).
*Anthocyanin coloration*.—RHS 58C (red purple group).
*Anthocyanin intensity*.—Ranges from weak to medium.
*Average length* (*mm*).—13.8.
*Average width* (*mm*).—9.6.

Fruiting truss characteristics:
*Anthocyanin coloration*.—N/A.
*Anthocyanin intensity*.—Absent or very weak.
*Average length at maturity* (*cm*).—20.5.
*Position relative to foliage*.—Beneath.
*Flower quantity* (*average per plant season long*).—45 to 55 (medium).
*Pedicel attitude of hairs*.—Upward.
*Pubescence*.—Weak.
*Attitude at first pick*.—Prostrate.

Flower characteristics:
*Petal color*.—RHS NN155C (white group).
*Sepal color*.—RHS 137A (green group).
*Corolla* (*flower*) *average diameter* (*mm*).—31.6 (large).
*Calyx average diameter* (*mm*).—37.3.
*Petal average length* (*mm*).—13.0.
*Petal average width* (*mm*).—12.2.
*Petal average length/width ratio*.—1.06 (ranges from as long as broad to longer than broad).
*Average petals per flower*.—5.5.
*Sepal average length* (*mm*).—15.1.
*Sepal average width* (*mm*).—5.4.
*Sepal average length/width ratio*.—2.81.
*Average sepals per flower*.—11.1.
*Size of calyx relative to corolla*.—Larger.
*Size of inner calyx relative to outer calyx*.—Same.
*Relative position of petals* (*flowers with* 5 *or* 6 *petals*).—Ranges from free to touching.

Reproductive organs:
*Receptacle color*.—RHS 147C (yellow green group).
*Pollen color*.—RHS 14A (yellow orange group).
*Stamen*.—Present.
*Pollen amount*.—Abundant.

Disease and pest reactions:
*Powdery mildew* (*sphaerotheca macularis*).—Moderate.
*Angular leaf spot* (*xanthomonas fragariae*).—Moderately susceptible.
*Botrytis fruit rot* (*botrytis cinerea*).—Moderately susceptible.
*Fusarium wilt* (*fusarium oxysporum*).—Resistant.
*Anthracnose crown rot* (*colletotrichum fragariae*).—Susceptible.
*Two-spotted spider mite* (*tetranychus urticae*).—Moderately susceptible.

We claim:

1. A new and distinct strawberry plant named 'BG-10.3181', as herein described and illustrated.

* * * * *